US011717513B2

(12) United States Patent
Fontaine et al.

(10) Patent No.: US 11,717,513 B2
(45) Date of Patent: Aug. 8, 2023

(54) MIRABEGRON FOR THE TREATMENT OF RETINAL DISEASES

(71) Applicants: SORBONNE UNIVERSITE, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR)

(72) Inventors: Valérie Fontaine, Cachan (FR); Cécile Vidal, Joinville-le-Pont (FR); José-Alain Sahel, Paris (FR)

(73) Assignees: SORBONNE UNIVERSITE, Paris (FR); CENTRE NATIONAL DE LA RECHERCHE SCIENTIFIQUE, Paris (FR); INSERM (INSTITUT NATIONAL DE LA SANTÉ ET DE LA RECHERCHE MÉDICALE), Paris (FR)

( * ) Notice: Subject to any disclaimer, the term of this patent is extended or adjusted under 35 U.S.C. 154(b) by 7 days.

(21) Appl. No.: 15/777,078

(22) PCT Filed: Nov. 17, 2016

(86) PCT No.: PCT/FR2016/052981
§ 371 (c)(1),
(2) Date: May 17, 2018

(87) PCT Pub. No.: WO2017/085407
PCT Pub. Date: May 26, 2017

(65) Prior Publication Data
US 2018/0353482 A1  Dec. 13, 2018

(30) Foreign Application Priority Data

Nov. 17, 2015 (FR) ...................................... 1561067

(51) Int. Cl.
*A61K 31/426* (2006.01)
*A61K 9/00* (2006.01)
*A61P 27/02* (2006.01)

(52) U.S. Cl.
CPC .......... *A61K 31/426* (2013.01); *A61K 9/0048* (2013.01); *A61K 9/0053* (2013.01); *A61P 27/02* (2018.01)

(58) Field of Classification Search
CPC .. A61K 31/352; A61K 31/426; A61K 9/0048; A61K 9/0053; A61K 2300/00; A61K 31/4439; A61K 31/427; A61K 45/06; A61K 31/506; A61K 31/192; A61K 31/496; A61K 31/216; A61K 31/4178; A61K 31/4704; A61K 31/5377; A61K 31/4709; A61K 9/2054; C07D 311/60; A61P 27/02

USPC ......................................................... 514/370
See application file for complete search history.

(56) References Cited

U.S. PATENT DOCUMENTS

| | | | | |
|---|---|---|---|---|
| 6,346,532 | B1 * | 2/2002 | Maruyama | C07D 213/30 514/252.1 |
| 6,441,047 | B2 * | 8/2002 | DeSantis, Jr. | A61K 31/445 514/649 |
| 7,094,895 | B2 * | 8/2006 | Baraldi | C07D 487/04 544/295 |
| 7,342,117 | B2 * | 3/2008 | Kawazoe | C07D 277/40 548/194 |
| 7,923,448 | B2 * | 4/2011 | Nedergaard | A61K 31/47 514/253.05 |
| 8,586,760 | B2 * | 11/2013 | Rao | A61K 31/426 548/194 |
| 8,828,966 | B2 * | 9/2014 | Mitchell | A61K 31/4439 514/47 |
| 9,029,407 | B2 * | 5/2015 | Rao | A61K 31/426 514/370 |
| 10,004,780 | B2 * | 6/2018 | Leveillard | A61K 9/0048 |
| 2006/0194756 | A1 * | 8/2006 | Borea | C07K 16/18 514/45 |
| 2009/0220516 | A1 * | 9/2009 | Laties | A61K 31/203 424/141.1 |
| 2009/0247483 | A1 * | 10/2009 | Mitchell | A61K 31/137 514/47 |
| 2011/0081426 | A1 * | 4/2011 | Rao | A61K 31/426 424/692 |
| 2013/0281498 | A1 * | 10/2013 | Rao | A61P 1/00 514/370 |
| 2014/0206729 | A1 * | 7/2014 | Peddy | A61P 13/00 514/370 |
| 2015/0224087 | A1 * | 8/2015 | Peddy | A61K 9/1635 514/370 |

FOREIGN PATENT DOCUMENTS

| EP | 1028111 | 8/2000 |
|---|---|---|
| WO | 2008042399 | 4/2008 |
| WO | 2010147830 | 12/2010 |

OTHER PUBLICATIONS

Nandakumar et al, "Lipofuscin and the Principles of Fundus Autofluorescence: a Review," Seminars in ophthalmology. 2012, 27(5-6):197-201.
Schmitz-Valckenberg et al, "Fundus Autofluorescence and Progression of Age-related Macular Degeneration," Survey of ophthalmology. 2009, 54(1):96-117.
Mahon et al, "Chloroquine causes lysosomal dysfunction in neural retina and RPE: Implications for retinopathy," Current Eye Research, 2004, 28:277-284.

(Continued)

*Primary Examiner* — Craig D Ricci
(74) *Attorney, Agent, or Firm* — Nixon & Vanderhye

(57) ABSTRACT

Disclosed is a method utilizing (R)-2-(2-aminothiazol-4-yl)-4'-[2-[(2-hydroxy-2-phenylethyl)amino]ethyl]acetic acid anilide or an analogue, pharmaceutically acceptable salt or solvate thereof for the treatment of a retinal disease, more specifically using mirabegron for the treatment of age-related macular degeneration. Also Disclosed is a pharmaceutical composition, a medicament and a kit for the treatment of age-related macular degeneration.

5 Claims, 2 Drawing Sheets

(56) References Cited

OTHER PUBLICATIONS

Anson, "The Estimation of Pepsin, Trypsin, Papain, and Cathepsin With Hemoglobin," the Journal of General Physiology, 1938, 22(1):79-89.
Steinle et al, "Beta3-Adrenergic Receptors Regulate Retinal Endothelial Cell Migration and Proliferation," the Journal of Biological Chemistry. 2003, 278(23):20681-20686.
Steinle et al, "Beta3-Adrenergic receptors mediate choroidal endothelial cell invasion, proliferation, and cell elongation," Experimental Eye Research, Academic Press LTD, London, 2005, 80(1):83-91.
International Search Report for Application No. PCT/FR2016/052981 dated Feb. 10, 2017.
Oikawa, F. et al., "Protective effects of the β3-adrenoceptor agonist CL316243 against N-methyl-D-aspartate-induced retinal neurotoxicity," Naunyn-Schmiedeberg's Arch Pharmacol (2012) 385:1077-1081.

\* cited by examiner

MIRABEGRON FOR THE TREATMENT OF RETINAL DISEASES

FIELD OF THE INVENTION

The present invention relates to the treatment of retinal diseases, such as age-related macular degeneration. The present invention relates in particular to the use of mirabegron or of one of the analogues, salts or solvates thereof for the treatment of a retinal disease, in particular for the treatment of age-related macular degeneration.

STATE OF THE RELATED ART

Age-related macular degeneration (AMD) is a major cause of blindness (in the legal sense) in developed countries and the most common eye disorder in the elderly. AMD is characterised by degeneration of the neuroepithelium in the macular region of the eye. Two major forms of advanced-stage AMD can be distinguished: neovascular AMD and atrophic AMD.

Neovascular AMD, described as wet or exudative, is manifested by a proliferation of new abnormal vessels under the retina. This phenomenon is referred to as "choroidal neovascularisation" or "CNV". These fragile new vessels allow the diffusion of serum, causing raising of the retina, and/or blood, inducing the onset of retinal bleeding. Neovascular AMD is the major cause of blindness in the elderly in industrialised countries. A number of treatments have been developed to improve the clinical status of patients, particularly with therapies targeting VEGFA, a powerful stimulant of angiogenesis and vascular permeability.

Atrophic AMD, also known as geographic atrophy or dry AMD, corresponds to the gradual disappearance of retinal pigment epithelium (RPE) cells, followed by that of the photoreceptors located at the level of the macula. This process creates holes of increasing size in the macula, visible by means of a mere retinal examination (optic fundus).

The incidence of neovascular AMD and atrophic AMD is comparable but the expansion of atrophic lesions and of the associated vision disorders are generally slower in the case of atrophic AMD. Between five and ten years generally elapse before the patient loses his/her central vision. At the present time, there is no approved therapy for preventing or treating atrophic AMD, essentially due to the lack of target molecule identification. Some studies have demonstrated that the consumption of vitamins E and C, betacarotenoids and zinc could slow down the development of atrophic AMD. However, the progression of the disease is not stopped.

Studies have demonstrated that the accumulation of lipofuscin, a cellular pigment composed of molecular debris, in RPE cells is a marker associated with the atrophic form of AMD (Nandakumar et al, Seminars in ophthalmology. 2012, 27(5-6): 197-201; Schmitz-Valckenberg et al, Survey of ophthalmology. 2009, 54(1): 96-117). A photoreceptor outer segment digestion defect by the RPE is the source of this accumulation and is probably linked with a decrease in lysosomal enzyme activity (Mahon et al, Curr Eye Res. 2004, 28:277-284). Indeed, the lysosomal enzyme activity is peak in a highly acidic pH range. An increase in the lysosomal pH of RPE cells thereby reduces this digestive process which is essential for proper retinal function.

The international patent application WO 2008/042399 describes a method for treating AMD by restoring an acidic lysosomal pH. This patent application also describes that adenosine or beta-adrenergic receptor stimulation could lower the lysosomal pH.

However, the Applicant has demonstrated that some molecules known to activate beta-adrenergic receptors, despite lowering the lysosomal pH of RPE cells, do not induce photoreceptor outer segment digestion (see Examples), and therefore are not suitable for treating AMD.

Furthermore, no molecule has yet been validated clinically at the present time.

As such, there is still a need to identify the molecules providing an optimal lysosomal activity so as to enable the breakdown of photoreceptor outer segments in RPE cells, thereby making it possible to prevent and/or treat AMD.

The Applicant has demonstrated, surprisingly, that some adrenergic receptor agonists, such as mirabegron, significantly reduce the accumulation of lipofuscin in RPE cells.

The present invention therefore relates to the use of mirabegron, or of an analogue, salt or solvate therefore for the treatment of a retinal disease, such as age-related macular degeneration.

SUMMARY

The present invention relates to an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof for use in the treatment of a retinal disease in a subject.

In one embodiment, said (R)-2-(2-aminothiazol-4-yl)-4'-[2-[(2-hydroxy-2-phenylethyl)amino]ethyl]acetic acid anilide is mirabegron, an analogue, a pharmaceutically acceptable salt or solvate thereof.

In one embodiment, said retinal disease is a disease affecting the macula. In one particular embodiment, said retinal disease is age-related macular degeneration, preferably atrophic age-related macular degeneration.

The present invention also relates to a pharmaceutical composition comprising an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof for use as described hereinabove and at least one pharmaceutically acceptable vehicle.

The present invention further relates to a medicament comprising an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof for use as described hereinabove.

In one embodiment, said pharmaceutical composition or said medicament according to the invention is intended to be administered to the subject in need thereof orally or topically.

The present invention also relates to a kit, comprising a compound, a pharmaceutical composition, or a medicament as described hereinabove.

In one embodiment, said kit is characterised in that it further comprises an apparatus for administering said compound, said pharmaceutical composition or said medicament to a subject in need thereof, and optionally the instructions for administering said compound, said pharmaceutical composition or said medicament to said subject.

Furthermore, the present invention relates to mirabegron for use in the treatment of AMD.

The present invention also relates to a method for treating a retinal disease in a subject in need thereof, said method comprising the administration to the subject of a therapeutically effective amount of an (R)-2-(2-aminothiazol-4-yl)-

4'-[2-[(2-hydroxy-2-phenylethyl)amino]ethyl]acetic acid anilide or an analogue or a pharmaceutically acceptable salt or solvate thereof.

According to one embodiment, said (R)-2-(2-aminothiazol-4-yl)-4'-[2-[(2-hydroxy-2-phenylethyl)amino]ethyl] acetic acid anilide is mirabegron, an analogue, a pharmaceutically acceptable salt or solvate thereof.

According to one embodiment, said retinal disease is a disease affecting the macula. According to one embodiment, said retinal disease is age-related macular degeneration, preferably atrophic age-related macular degeneration.

DEFINITIONS

In the present invention, the terms below are defined as follows:

A "pharmaceutically acceptable salt" of the compound of the invention includes the acid or base addition salts of said compound. Suitable acid addition salts are formed using acids which form non-toxic salts. Examples of acid addition salts include, but are not limited to, acetate, trifluoroacetate, adipate, aspartate, benzoate, besylate, bicarbonate/carbonate, bisulphatesulphate, borate, tetrafluoroborate, camsylate, citrate, cyclamate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, pyroglutamate, saccharate, stearate, succinate, tannate, tartrate, tosylate, trifluoroacetate and xinofoate salts. Suitable base addition salts are formed using bases which form non-toxic salts. Examples of base addition salts include, but are not limited to, aluminium, arginine, benzathine, calcium, choline, diethylamine, diolamine, glycine, lysine, magnesium, meglumine, olamine, potassium, sodium, tromethamine, 2-(diethylamino)ethanol, ethanolamine, morpholine, 4-(2-hydroxyethyl)morpholine and zinc salts. Preferably, the pharmaceutically acceptable salt include the hydrochloride/chloride, hydrobromide/bromide, bisulphate/sulphate, nitrate, citrate, and acetate.

The term "solvate" is used in the present invention to describe a compound of the invention comprising stoichiometric or sub-stoichiometric quantities or one or of more than one pharmaceutically acceptable molecules such as ethanol.

The term "subject" relates to a mammal, preferably a human. In one embodiment, the subject may be a "patient", i.e. a warm-blooded animal, preferably a human, who is awaiting the receipt of, or is receiving medical care, having undergone a medical procedure, or monitored for the development of retinal disease. In one embodiment, the subject is an adult, for example a subject over 18 years of age. In another embodiment, the subject is a child, for example a subject under 18 years of age. In one embodiment, the subject is a man. In another embodiment, the subject is a woman.

The terms "treatment" or "treat" refer both to therapeutic treatment and prophylactic or preventive measures, intended to prevent or slow down the progression of a retinal disease. The subjects in need of treatment include those who already have a retinal disease, those predisposed to a retinal disease and those in whom a retinal disease is to be prevented. A subject is successfully treated for a retinal disease if, after having received a therapeutically effective amount of a compound of the invention, the patient exhibits an observable or measurable reduction, or the absence, of at least one of the following points: reduction of the number of pathogenic cells, reduction of the percentage of pathogenic cells with respect to the total cells, and/or of one or more of the symptoms associated with retinal disease, an improvement in visual acuity or an improvement in quality of life. The above evaluation parameters are easily measurable using routine procedures familiar to a physician.

The term "vehicle" relates to a substance carrying the product of interest in a composition, in particular this may be a substance suitable for dissolving same. The vehicle may for example be water.

A "pharmaceutically acceptable vehicle" relates to a vehicle that does not produce an adverse, allergic or undesirable reaction when administered to a subject. This includes all solvents, dispersion media, coatings, antibacterial and antifungal agents, isotonic agents, delayed absorption agents and further similar substances. For administration to a human, the preparations must meet criteria in respect of sterility, pyrogenicity, and the general safety and purity standards required by regulatory offices such as the FDA or EMA.

A "therapeutically effective amount" relates to the necessary and sufficient amount of therapeutic agent, without causing significant negative or undesirable effects, to (1) delay or prevent the onset of retinal disease; (2) reduce or stop the progression, worsening or deterioration of one or more of the symptoms of retinal disease; (3) relieve or make improvements to the symptoms of retinal disease; (4) reduce the severity or incidence of retinal disease, and/or (5) cure retinal disease. A therapeutically effective amount may be administered prior to the onset of retinal disease, for a preventive or prophylactic action. Alternatively or additionally, the therapeutically effective amount may be administered after the onset of retinal disease, for a therapeutic action.

"About", preceding a figure, means more or less 10% of the nominal value of this figure.

DETAILED DESCRIPTION

The present invention relates to the use of a compound for the treatment of retinal disease in a subject in need thereof, said compound being an adrenergic receptor agonist.

Preferably, in one embodiment, the compound of the invention is a beta 1, 2 or 3 adrenergic receptor agonist, preferably beta 3.

In one embodiment, the compound of the invention is an (R)-2-(2-aminothiazol-4-yl)-4'-[2-[(2-hydroxy-2-phenylethyl)amino]ethyl]acetic acid anilide or an analogue, a pharmaceutically acceptable salt or solvate thereof.

Herein, the (R)-2-(2-aminothiazol-4-yl)-4'-[2-[(2-hydroxy-2-phenylethyl)amino]ethyl]acetic acid anilide is also referenced under the term mirabegron. Therefore, in one embodiment, the compound of the invention is mirabegron.

The Applicant has in particular demonstrated that mirabegron lowers the lysosomal pH at low concentrations (1 pM, see Examples and FIG. 1). Furthermore, the Applicant has demonstrated that mirabegron significantly restores the activity of cathepsin D, a lysosomal proteolytic enzyme requiring an acidic pH for the activity thereof (see Examples and FIG. 2). These results were confirmed in a cellular lipofuscin accumulation model. Indeed, the Applicant demonstrated that mirabegron reduces the accumulation of lipofuscin from 2 weeks of treatment (see Examples and FIG. 3). Therefore, the Applicant has demonstrated the therapeutic potential of this molecule for the treatment of AMD.

The invention therefore relates to mirabegron or an analogue, a pharmaceutically acceptable salt or solvate thereof for use in the treatment of a retinal disease.

Mirabegron has the following general formula:

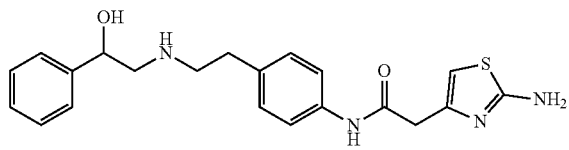

Mirabegron is also known as Betmiga™, Betanis™ or Myrabetriq™.

Examples of analogues of mirabegron include, without being limited thereto, the compounds described in the U.S. Pat. No. 6,346,532.

Therefore, in one embodiment of the invention, the analogue of mirabegron has the following general formula (I):

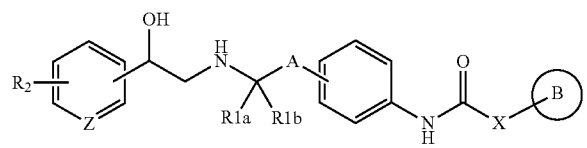

wherein:
  the ring B represents a heteroaryl group optionally substituted and optionally merged with a benzene ring;
  X represents a bond, a lower alkylene or a lower alkenylene optionally substituted by a hydroxy group or a lower alkyl group, a carbonyl, or a group represented by —NH— (where X is a lower alkylene group optionally substituted by a lower alkyl group, the hydrogen atoms bound with the carbon forming the ring B may form a lower alkylene group with the lower alkyl group, thereby forming a ring);
  A represents a lower alkylene or a group represented by—lower alkylene-O—;
  R1a and R2a may be identical or different, each representing a hydrogen atom or a lower alkyl group;
  R2 represents a hydrogen atom or a halogen atom; and
  Z represents a nitrogen atom or a group represented by =CH—.

Herein, the term "lower" means a linear or branched hydrocarbon chain having 1 to 6 carbon atoms, unless specified otherwise.

Examples of "lower alkyl group" include, but are not limited to, methyl, ethyl, linear or branched propyl, linear or branched butyl, linear or branched pentyl, and linear or branched hexyl, preferably the lower alkyl group is an alkyl having 1 to 4 carbon atoms, and particularly methyl, ethyl, propyl and isopropyl.

A non-limiting example of a "lower alkylene group" is a divalent group obtained by subtracting an arbitrary number of hydrogen atom(s) from the "lower alkyl group" defined hereinabove, preferably an alkylene group having 1 to 4 carbon atoms, and particularly methylene, ethylene, propylene and butylene.

Examples of "lower alkenylene group" include, but are not limited to, the vinylene, propenylene, butenylene, pentenylene and hexenylene groups.

Herein, the "heteroaryl group optionally merged with a benzene ring" in the "heteroaryl group optionally substituted or optionally merged with a benzene ring" means a cyclic group wherein the benzene ring is merged with a heteroaryl group as described hereinafter or a non-merged heteroaryl group.

Examples of "cyclic groups wherein the benzene ring is merged with a heteroaryl group" include, but are not limited to, quinolyl, isoquinolyl, quinazolinyl, quinolidinyl, quinoxalinyl, cinnolinyl, benzimidazolyl, imidazopyridyl, benzofuranyl, benzoisoxazolyl, benzoxazolyl, benzothiazolyl, oxazolopyridyl, isothiazolopyridyl and benzothiazolyl; and rings supplemented with oxygens such as oxobenzofurayl.

Examples of "non-merged heteroaryl group" include, but are not limited to, monocyclic heteroaryl groups such as furyl, thienyl, pyrrolyl, imidazolyl, thiazolyl, pyrazolyl, isothiazolyl, pyridyl, pyrimidyl, pyridazinyl, pyrazinyl, thiadiazolyl, triazolyl and tetrazolyl; and the bicyclic heteroaryl groups such as naphthylidinyl and pyridopyrimidinyl.

The substituent in the "heteroaryl group optionally substituted and optionally merged with a benzene ring" may be any group usually substituted on this cyclic group. Examples include, but are not limited to, a halogen atom, a lower alkyl, a lower alkenyl, a lower alkynyl, a hydroxy, sulfanyl, halogen-lower alkyl, lower alkyl-O—, lower alkyl-S—, lower alkyl-O—CO—, carboxy, sulfonyl, sulfinyl, lower alkyl-SO—, lower alkyl-SO$_2$—, lower alkyl-CO—, lower alkyl-CO—O—, carbamoyl, lower alkyl-NH—CO—, di-lower alkyl —N—CO—, nitro, cyano, amino, guanidino, lower alkyl-CO—NH—, lower alkyl-SO$_2$—NH—, lower alkyl-NH—, di-lower alkyl —N—, O-lower alkylene —O— group and further similar groups.

These substituents may also be substituted by a substituent such as an aryl group, a heteroaryl group, a halogen atom, a hydroxy, sulfanyl, halogen-lower alkyl, lower alkyl-O—, lower alkyl-S—, lower alkyl-O—CO—, carboxy, sulfonyl, sulfinyl, lower alkyl-SO—, lower alkyl-SO$_2$—, lower alkyl-CO—, lower alkyl-CO—O—, carbamoyl, lower alkyl-NH—CO—, di-lower alkyl-N—CO—, nitro, cyano, amino, guanidino, lower alkyl-CO—NH—, lower alkyl-SO$_2$—NH, lower alkyl-NH—, di-lower alkyl-N— group and further similar groups. These substituents such as an aryl group, a heteroaryl or other group may also be substituted by a halogen atom, etc.

The "lower alkenyl group" is a linear or branched alkenyl group having 2 to 6 carbon atoms. Examples includes, but are not limited to, vinyl, propenyl, butenyl, pentenyl, and hexenyl.

The "lower alkynyl group" is a linear or branched alkynyl group having 2 to 6 carbon atoms. Examples include, but are not limited to, ethynyl, propynyl, butynyl, pentynyl and hexynyl.

The term "halogen atom" means a fluorine atom, a chlorine atom, a bromine atom or an iodine atom. The term "halogen-lower alkyl group" means a group wherein one (or more) hydrogen atom(s) of the alkyl group described hereinabove, chosen arbitrarily, is (are) substituted by one (or more) halogen atom(s).

The case wherein X is a bond means that the carbon atom of the —CO— group is bonded directly to the ring B.

The compound according to the invention, preferably mirabegron or an analogue, comprises at least one asymmetric carbon atom. As such, there are optical isomers such as compounds of configuration (R) or (S), racemates, diastereoisomers, etc. The present invention includes all of the isomers, each of the separate isomers and the mixtures thereof. The present invention also includes hydrates, solvates (such as ethanol solvates) and polymorphic substances of the compound of the invention, mirabegron or one of the analogues thereof.

Preferably, in one embodiment, the analogue of mirabegron has the following general formula (Ia):

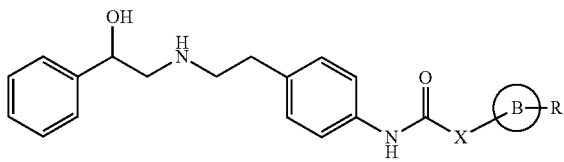

wherein:
the ring B represents a heteroaryl group;
X represents a bond or a lower alkylene group;
R represents a hydrogen atom, a halogen atom, a lower alkylene group, a nitrogenous group, a lower alkyl aryl group, or a halogen-lower alkyl aryl group; or a salt thereof.

Preferably, in one embodiment, the analogue of mirabegron is selected from the group comprising (R)-4'-[2-[(2-Hydroxy-2-phenylethyl)amino]ethyl]-2-pyridinecarboxyanilide, (R)-2-[1-(4-chlorobenzyl)-1H-imidazol-2-yl)-4'-[2-[(2-hydroxy-2-phenylethyl)amino]ethyl]-acetanilide, (R)-2-[1-(3,4-dichlorobenzyl)-1H-tetrazol-5-yl]-4'-[2-[(2-hydroxy-2-phenylethyl)amino]ethyl]acetanilide, (R)-2-(2-aminothiazol-4-yl)-4'-[2-(2-hydroxy-2-phenylethyl)amino]ethyl]acetanilide, (R)-2-(2-benzyl-1H-1,2,4-triazol-3-yl)-4'-[2-[(2-hydroxy-2-phenylethyl)-amino]ethyl]acetanilide, (R)-2-(2-aminopyridin-6-yl)-4'-[2-[(2-hydroxy-2-phenylethyl)amino]ethyl]acetanilide, (R)-4'-[2-[(2-hydroxy-2-phenylethyl)amino]ethyl]-2-(2-pyridyl)acetanilide, (R)-4'-[2-[(2-hydroxy-2-phenylethyl)-amino]ethyl]-2-(2-pyrazinyl)acetanilide, and (R)-4'-[2-[(2-hydroxy-2-phenylethyl)amino]ethyl)-2-(2-pyrimidinyl)-acetanilide, or one of the salts thereof.

In one embodiment, the (R)-2-(2-aminothiazol-4-yl)-4'-[2-[(2-hydroxy-2-phenylethyl)amino]ethyl]acetic acid anilide or an analogue, a pharmaceutically acceptable salt or solvate thereof is not in heavy or deuterated form. In one particular embodiment, mirabegron is non-deuterated.

In one embodiment, mirabegron is in crystalline form. In one particular embodiment, mirabegron is in alpha crystalline form. In another particular embodiment, mirabegron is in beta crystalline form. The alpha and beta crystalline forms of mirabegron have a free base and have specific physicochemical characteristics. The alpha and beta crystalline forms of mirabegron are described in the U.S. Pat. No. 7,342,117.

Herein, the term "retinal disease" includes the various disorders liable to affect the retina which is the layer of nerve cells covering the back of the eye.

Examples of disorders affecting the retina include, but are not limited to, age-related macular degeneration (AMD), Stargardt disease, diabetic retinopathy, and pigmentary retinitis.

In one embodiment, the retinal disease according to the invention is a disease affecting the macula, i.e. the central region of the retina. Examples of diseases affecting the macula include, but are not limited to, age-related macular degeneration and Stargardt disease.

In one embodiment, the retinal disease according to the invention is age-related macular degeneration or Stargardt disease.

In one embodiment, the retinal disease according to the invention is age-related macular degeneration.

In one embodiment, the age-related macular degeneration according to the invention is at the early stage, also known as age-related maculopathy. Early-stage age-related macular degeneration is characterised by the accumulation in and around the macula of photoreceptor function debris (known as "drusen"), associated with pigmented spots (alterations of the pigment epithelium).

In another embodiment, the age-related macular degeneration according to the invention is at the late stage. Late stages are characterised by uni- or bilateral complications. Two forms are then distinguished, exudative or atrophic.

In one embodiment, the age-related macular degeneration is of the atrophic type, also known as dry AMD.

In another embodiment, the retinal disease of the invention is Stargardt disease. Stargardt disease is a hereditary macular dystrophy, manifesting in children between 7 and 12 years of age generally.

In one embodiment, the subject suffers from a retinal disease, preferably AMD or Stargardt disease. In one embodiment, the subject suffers from early-stage AMD. In another embodiment, the subject suffers from late-stage AMD.

In another embodiment, the subject is liable to suffer from a retinal disease, preferably AMD. In one embodiment, the subject is an at-risk subject for the onset of the retinal disease according to the invention. Examples of risks include, but are not limited to, heredity (present or previous existence of other cases of retinal disease, preferably AMD, in the subject's family), smoking, age, sun exposure, an imbalanced diet (for example low intake of green vegetables and omega-3 fatty acids), a high blood cholesterol concentration, high blood pressure, and similar factors.

In one embodiment, the subject has not previously been treated with another treatment for the retinal disease according to the invention. In another embodiment, the subject has previously been treated with another treatment for the retinal disease according to the invention.

In one embodiment, the subject is a human over 45 years of age. In another embodiment, the subject is a human under 18 years of age.

The present invention also relates to a composition comprising a compound according to the invention.

In one embodiment, the composition according to the invention comprises an anilide of (R)-2-(2-aminothiazol-4-yl)-4'-[2-[(2-hydroxy-2-phenylethyl)amino]ethyl]acetic acid or an analogue or a pharmaceutically acceptable salt or solvate thereof, preferably mirabegron.

In one embodiment, the composition of the invention is used for the treatment of a retinal disease, preferably age-related macular degeneration.

The present invention further relates to a pharmaceutical composition comprising a compound of the invention and at least one pharmaceutically acceptable vehicle.

In one embodiment, the pharmaceutical composition of the invention comprises an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof, preferably mirabegron, and at least one pharmaceutically acceptable vehicle.

In one embodiment, the pharmaceutical composition according to the invention is used for the treatment of a retinal disease, preferably age-related macular degeneration.

The present invention also relates to a medicament comprising a compound according to the invention.

In one embodiment, the medicament according to the invention comprises an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof according to the invention, preferably mirabegron, a composition or a pharmaceutical composition according to the present invention.

In one embodiment, the medicament according to the invention is used for the treatment of a retinal disease, preferably age-related macular degeneration.

Preferably, the composition, the pharmaceutical composition or the medicament of the present invention comprise a therapeutically effective amount of a compound according to the invention, preferably an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof, preferably mirabegron.

In one embodiment, the (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof according to the present invention, preferably mirabegron, is used in combination with at least one other therapeutic agent for treating a retinal disease, preferably age-related macular degeneration.

Examples of other therapeutic agents for treating age-related macular degeneration include, but are not limited to, anti-vasoproliferative agents such as ranibizumab (lucentis) or bevacizumab (avastin), anti-angiogenic agents such as VEGF trap (regeneron), bevasiranib or tyrosine kinase inhibitors.

In one embodiment, the therapeutically effective amount ranges from about 1 to 10000 mg/mL of composition, pharmaceutical composition or medicament of the invention, preferably from about 5 to about 5000 mg/mL, preferably from about 10 to about 2000 mg/mL, preferably from about 20 to about 100 mg/mL of composition, pharmaceutical composition or medicament according to the invention.

In one embodiment, the therapeutically effective amount ranges from about 1 to 10000 mg/g of composition, pharmaceutical composition or medicament according to the invention, preferably from about 5 to about 5000 mg/g, preferably from about 10 to about 2000 mg/g, preferably from about 20 to about 100 mg/g of composition, pharmaceutical composition or medicament according to the invention.

It is understood that the total daily usage of the (R)-2-(2-aminothiazol-4-yl)-4'-[2-[(2-hydroxy-2-phenylethyl)amino]ethyl]acetic acid or analogue or pharmaceutically acceptable salt or solvate thereof, preferably mirabegron, of the composition, pharmaceutical composition or medicament of the invention will be adjusted by the attending physician within the framework of his/her medical opinion. The therapeutically effective dose specific to each patient will depend on a variety of factors including the disorder treated and the severity thereof; the activity of the compound used; the specific composition used; the patient's age, weight, general state of health, sex and diet, the duration and mode of administration; the duration of the treatment; the medicament used in combination or concomitantly with the compound used, and other similar factors known in the medical field. For example, it is routine in this field to start with compound doses lower than the recommended doses to achieve the desired therapeutic effect and gradually increase the dosage until the effect has been achieved. However, the daily dosage of compounds may vary over a wide range from about 1 to about 10000 mg per adult per day, preferably from about 5 to about 5000, preferably from about 10 to about 2000 mg, more preferentially from about 20 to about 100 mg per adult per day. Preferably, the composition comprises 1, 10, 20, 50, 100, 250, 500, 1000 and 2000 mg of the active ingredient for the symptomatic adjustment of the dosage to be administered to the patient to be treated. A medicament typically contains from about 1 to about 10000 mg of active ingredient, preferably from 5 to 5000, preferably from 10 to 2000 mg of active ingredient. An effective amount of the medicament is ordinarily supplied at a dose ranging from about 0.01 mg/kg to about 100 mg/kg of body weight per day, preferably from about 0.05 mg/kg to about 40 mg/kg, preferably from about 0.1 mg/kg to 20 mg/kg of body weight per day, more preferentially from about 0.2 to about 1 mg/kg of body weight per day.

In one embodiment, the daily dose of the compound of the invention, preferably mirabegron, composition, pharmaceutical composition or medicament of the present invention is adjusted according to the subject's potential kidney and/or liver disorders.

In one embodiment, the total daily dose of (R)-2-(2-aminothiazol-4-yl)-4'-[2-[(2-hydroxy-2-phenylethyl)amino]ethyl]acetic acid anilide or the analogue or pharmaceutically acceptable salt or solvate thereof, preferably mirabegron, ranges from about 1 mg to about 100 mg, preferably from about 10 mg to about 80 mg, preferably from about 20 mg to about 60 mg.

In one particular embodiment, the initial total daily dose of (R)-2-(2-aminothiazol-4-yl)-4'-[2-[(2-hydroxy-2-phenylethyl)amino]ethyl]acetic acid anilide or the analogue or pharmaceutically acceptable salt or solvate thereof, preferably mirabegron, ranges from about 10 mg to about 50 mg, preferably from about 20 mg to about 30 mg, preferably is of about 25 mg. In another particular embodiment, the total daily maintenance dose of (R)-2-(2-aminothiazol-4-yl)-4'-[2-[(2-hydroxy-2-phenylethyl)amino]ethyl]acetic acid anilide or the analogue or pharmaceutically acceptable salt or solvate thereof, preferably mirabegron, ranges from about 20 mg to about 80 mg, preferably from about 40 mg to about 60 mg, preferably about 50 mg.

In one particular embodiment, the (R)-2-(2-aminothiazol-4-yl)-4'-[2-[(2-hydroxy-2-phenylethyl)amino]ethyl]acetic acid anilide or the analogue or pharmaceutically acceptable salt or solvate thereof, preferably mirabegron, the composition, pharmaceutical composition or medicament of the invention is administered at a dose of about 25 mg. In another particular embodiment, the (R)-2-(2-aminothiazol-4-yl)-4'-[2-[(2-hydroxy-2-phenylethyl)amino]ethyl]acetic acid anilide or the analogue or pharmaceutically acceptable salt or solvate thereof, preferably mirabegron, the composition, pharmaceutical composition or medicament according to the invention is administered at a dose of about 50 mg.

In one embodiment, the medicament of the invention contains about 25 mg of the compound, composition or pharmaceutical composition of the invention. In another embodiment, the medicament of the invention contains about 50 mg of the compound, composition or pharmaceutical composition of the invention.

In one embodiment, the compound according to the invention, preferably an (R)-2-(2-aminothiazol-4-yl)-4'-[2-[(2-hydroxy-2-phenylethyl)amino]ethyl]acetic acid anilide or the analogue or pharmaceutically acceptable salt or solvate thereof, preferably mirabegron, the composition, pharmaceutical composition or medicament according to the invention, alone or in combination with another therapeutic agent, may be administered in unitary dosage form, in a mixture with conventional pharmaceutical substrates, to animals and to humans. Suitable unitary administration forms comprise oral administration forms such as tablets, hard capsules, powders, granule and oral suspensions or solutions, sublingual or buccal administration forms, sprays, implants, subcutaneous, transdermal, topical, intraperitoneal, intravenous, intrathecal, intraocular and intranasal administration forms, and rectal administration forms.

In one embodiment, the composition, pharmaceutical composition or medicament of the present invention comprises one or more pharmaceutically acceptable vehicles for a formulation suitable for oral administration.

Examples of forms suitable for oral administration include, but are not limited to, tablets (including sustained-release tablets), hard capsules, powders, pills (including sugar-coated pills), capsules (including soft gelatin capsules), oral suspensions, oral solutions, and other similar forms.

In one embodiment, the composition, pharmaceutical composition or medicament of the present invention comprises one or more pharmaceutically acceptable vehicles for a formulation suitable for topical administration. In one particular embodiment, the composition, pharmaceutical composition or medicament according to the present invention comprises one or more pharmaceutically acceptable vehicles for a formulation suitable for topical administration in the eye.

Examples of forms suitable for topical administration include, but are not limited to, compositions in liquid, paste, or solid form, and, more particularly, in the form of aqueous solutions, collyriums, drops, dispersions, sprays, or microcapsules, micro- or nanoparticles or polymer or gel patches enabling a controlled release.

In one embodiment, the composition, pharmaceutical composition or medicament of the present invention comprises one or more pharmaceutically acceptable vehicles for a formulation suitable for being injected. In one particular embodiment, the composition, pharmaceutical composition or medicament of the present invention has a form suitable for intraocular injection, preferably for intravitreal injection.

Examples of forms suitable for administration by injection include, but are not limited to, sterile aqueous solutions, dispersions, emulsions, suspensions, solid forms suitable for preparing solutions or suspensions by adding a liquid before use such as, for example, powders.

In one embodiment, the compound according to the invention, preferably an (R)-2-(2-aminothiazol-4-yl)-4'-[2-[(2-hydroxy-2-phenylethyl)amino]ethyl]acetic acid anilide or the analogue or the pharmaceutically acceptable salt or solvate thereof, preferably mirabegron, the composition, pharmaceutical composition or medicament of the present invention is administered to the subject at least once per day. For example, the compound, composition, pharmaceutical composition or medicament according to the invention may be administered once per day, twice or three times per day. Preferably, the compound, composition, pharmaceutical composition or medicament of the invention is administered once per day.

In another embodiment, the compound according to the invention, preferably an (R)-2-(2-aminothiazol-4-yl)-4'-[2-[(2-hydroxy-2-phenylethyl)amino]ethyl]acetic acid anilide or the analogue or the pharmaceutically acceptable salt or solvate thereof, preferably mirabegron, the composition, pharmaceutical composition or medicament of the present invention is administered to the subject at least once per week. For example, the compound, composition, pharmaceutical composition or medicament of the invention may be administered once per week, twice, three times, four times or up to seven times per week.

In another embodiment, the compound according to the invention, preferably an (R)-2-(2-aminothiazol-4-yl)-4'-[2-[(2-hydroxy-2-phenylethyl)amino]ethyl]acetic acid anilide or the analogue or the pharmaceutically acceptable salt or solvate thereof, preferably mirabegron, the composition, pharmaceutical composition or medicament according to the present invention is administered to the subject at most once per month. For example, the compound, composition, pharmaceutical composition or medicament according to the invention may be administered once per month, once every two months, once per quarter, twice yearly or once yearly.

The present invention also relates to a method for treating a retinal disease, preferably age-related macular degeneration, in a subject in need thereof comprising the administration to the subject of a therapeutically effective amount of a compound according to the invention as described hereinabove, preferably an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof, preferably mirabegron.

In one embodiment, the composition, pharmaceutical composition or medicament according to the invention is administered to the subject.

The present invention also relates to a method for lowering the lysosomal pH in retinal pigment epithelium cells comprising the administration of a composition comprising a compound according to the invention as described hereinabove, preferably an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof, preferably mirabegron.

The present invention further relates to a method for increasing the digestion of photoreceptor outer segments of the retinal pigment epithelium comprising the administration of a composition comprising a compound according to the invention as described hereinabove, preferably an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof, preferably mirabegron.

The present invention also relates to a method for lowering lipofuscin accumulation in retinal pigment epithelium cells comprising the administration of a composition comprising a compound according to the invention as described hereinabove, preferably an (R)-2-(2-aminothiazol-4-yl)-4'-[2-[(2-hydroxy-2-phenylethyl)amino]ethyl]acetic acid anilide or an analogue or a pharmaceutically acceptable salt or solvate thereof, preferably mirabegron.

The present invention also relates to a kit comprising an (R)-2-(2-aminothiazol-4-yl)-4'-[2-[(2-hydroxy-2-phenylethyl)amino]ethyl]acetic acid or an analogue or a pharmaceutically acceptable salt or solvate thereof, a composition, pharmaceutical composition or medicament as described hereinabove.

In one embodiment, the kit also comprises an apparatus used for administering the compound, composition, pharmaceutical composition or medicament to a subject.

In one embodiment, the kit further comprises instructions for administering the compound, composition, pharmaceutical composition or medicament to said subject.

In one embodiment, the kit comprises an additional therapeutic agent. In one embodiment, the additional therapeutic agent is another agent for the treatment of the retinal disease according to the invention.

In one embodiment, the additional therapeutic agent has a form suitable for the same route of administration as the compound, composition, pharmaceutical composition or medicament of the invention. In another embodiment, the additional therapeutic agent has a form suitable for a different route of administration to that of the compound, composition, pharmaceutical composition or medicament according to the invention.

EXAMPLES

Figure 1:
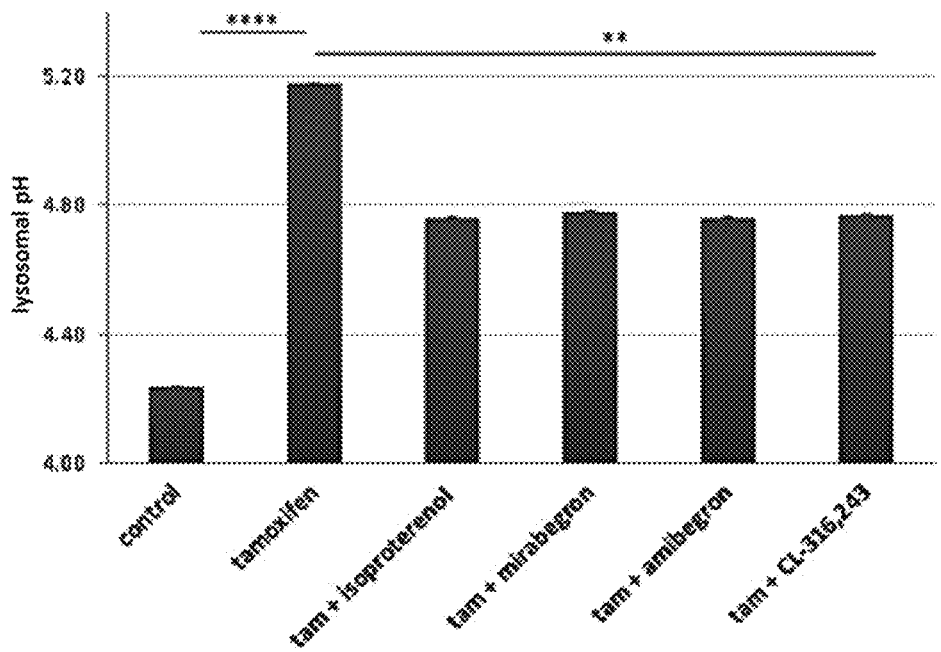
FIG. 1 is a histogram showing the effect of the adrenergic receptor agonists isoproterenol, mirabegron, amibegron and CL-316,243 on the lysosomal pH of cells treated with tamoxifen. The results were compared statistically by means of an ANOVA and a Dunnett's test. **$p<0.0001$, $p<0.01$.

The present invention will be understood more clearly on reading the following examples illustrating the invention in a non-limiting manner.

Example 1

Materials and Methods
Primary Porcine RPE Culture

Pigs' eyes are delivered to Institut de la Vision in a cold medium from a local slaughterhouse. The eyes are dissected so as to remove the anterior segment of the eye, the vitreous body and the neural retina. The eyeballs are then washed twice with PBS, filled with trypsin (0.25% in PBS) and incubated at 37° C. for 1 hr15. The RPE cells are then retrieved by repeated pipetting, centrifuged to remove the trypsin, and resuspended in DMEM culture medium supplemented with 20% foetal calf serum (DMEM20% FCS). The cells of each eye are then inoculated in a 6 cm diameter Petri dish, cultured in an atmosphere containing 5% CO2 at 37° C., and the culture medium is replaced after 24 hours and 4 days in vitro. After one week, the cells reach confluency and can then be passaged.

Alkalinisation and Measurement of Lysosomal pH ($pH_L$) of RPE

After one week in culture, the cells are treated with trypsin and transferred to a 96-well plate with a black background at a cell density of $1.5 \times 10^5$ cells/cm² in DMEM2% FCS. After 24 hours, the cells are treated with a beta-adrenergic agonist (mirabegron, amibegron, clenbuterol or isoproterenol at 1 pM or CL-316,243 at 20 nM), and 5 minutes later with tamoxifen (15 µM), and the $pH_L$ is measured after a further 20 minutes. This measurement is made using a coloured indicator (Lysosensor Yellow/BlueDND-160) exhibiting excitability at 329 and 384 nm and suitable for measuring pH variations in acidic organelles independent of the dye concentration. To measure the $pH_L$, the cells are incubated with the dye for 5 minutes at 37° C., and the fluorescence emitted by the dye is measured on a plate reader. The excited light ratio at 329/384 nm is then converted into pH using a calibration series (pH 4 to pH 6) performed in a KCl buffer in the presence of 10 µM of monensin and 20 µM of nigericin, two ionophores.

Cathepsin D Activity Measurement

After one week in culture, the cells are treated with trypsin and transferred into 3.5 cm diameter Petri dishes at a cell density of $1.5 \times 10^5$ cells/cm² in DMEM2% FCS. After 24 hours, the cells are treated with 20 nM of concanamycin so as to inhibit the activity of cathepsin D, as well as with a beta-adrenergic agonist. After 24 hours of treatment, the cells are washed with PBS and then transferred into an extraction buffer on ice. The cell extract is centrifuged at 2000 rpm at 4° C. for 10 minutes and the supernatant corresponding to the cytosolic part is frozen at −80° C. until the measurement of the enzyme activity. The activity of cathepsin D is measured using the Anson method (J Gen Physiol. 1938, 22(1):79-89) that we adapted to our experimental schedule. In brief, the cytosolic extract is incubated for 10 minutes at 37° C. in a haemoglobin solution (2.5% in 400 mM of citrate buffer at pH 2.8). The reaction is stopped by adding 5% trichloroacetic acid and the mixture is centrifuged. The optical density of the supernatant containing the breakdown products of haemoglobin is measured at 280 nm. The absorbance is corrected by subtracting that of the control, prepared as above but by adding haemoglobin after stopping the enzymatic reaction. One unit of cathepsin D is then defined as being the quantity of enzyme required to induce a change of absorbance of 1 to 280 nm for 60 minutes of incubation using the experimental conditions described hereinabove. The protein concentration of the cell lysates is measured according to the Bradford method so as to normalise the results.

Porcine Photoreceptor Outer Segment (POS) Preparation

Pig retinas are sampled in a darkroom under red light. The POS are separated from the retinas on a sucrose gradient as described hereinafter. In brief, the pig retinas are homogenised in a solution containing 20% sucrose, 20 mM of Tris-acetate at pH 7.2, 2 mM of MgCl2, 10 mM of glucose and 5 mM of taurine. The samples are then deposited on a continuous sucrose gradient (25 to 60%) containing 20 mM of Tris acetate at pH 7.2, 10 mM of glucose and 5 mM of taurine, and centrifuged at 25000 rpm at 4° C. for 2 hrs. The pink bands obtained correspond to the POS and are then sampled and frozen at −80° C. until use.

In order to obtain oxidised POS (POS-ox), the POS are exposed to ultra-violet ($\lambda=312$ nm) for 3 hrs. They are then washed in PBS, centrifuged at 5000 rpm and resuspended in DMEM20% FCS containing 2.5% sucrose.

In Vitro Model of Lipofuscin Accumulation in RPE

After one week in culture, the cells are treated with trypsin and transferred into a 96-well plate with a light background at a cell density of $1.5 \times 10^5$ cells/cm² in DMEM2% FCS.

In order to induce an accumulation of lipofuscin type material in the RPE cells, the latter are treated 3 times per week with $5 \times 10^6$ POS-ox in DMEM20% FCS containing 2.5% of sucrose for two weeks. In parallel, the cells are treated, or not, with a beta-adrenergic antagonist. The autofluorescence induced by the accumulation of lipofuscin is measured using a plate reader (excitation at 480 nm and emission between 500 and 700 nm corresponding to the emission spectrum of lipofuscin).

Results

Effect of Agonists on Lysosomal DH

The molecules tested in the experiments consist of three specific beta-3 adrenergic receptor agonists (Mirabegron, Amibegron, CL-316,243), and a non-specific agonist (isoproterenol).

These molecules were tested in a cellular lysosomal pH alkalinisation model of the RPE induced by treating the cells with 15 µM of tamoxifen and inducing an increase in the pH of the order of 1 pH unit in 20 minutes.

All the molecules tested made it possible to obtain a maximum effect of almost 50% on the re-acidification of the pH to 1 pM with the exception of CL-316,243 effective from 20 nM (FIG. 1).

Effect of Agonists on Cathepsin D Activity

Cathepsin D is the lysosomal proteolytic enzyme mainly present in the retinal pigment epithelium involved in photoreceptor outer segment digestion. The activity thereof is dependent on the protonation of the amino acid aspartic acid of the active site thereof and on the conformation thereof, which both require an acidic environment. As such, the study of the effect of the molecules tested on the activity of cathepsin D makes it possible to determine the effect of these molecules on lysosomal enzyme activity.

Figure 2:
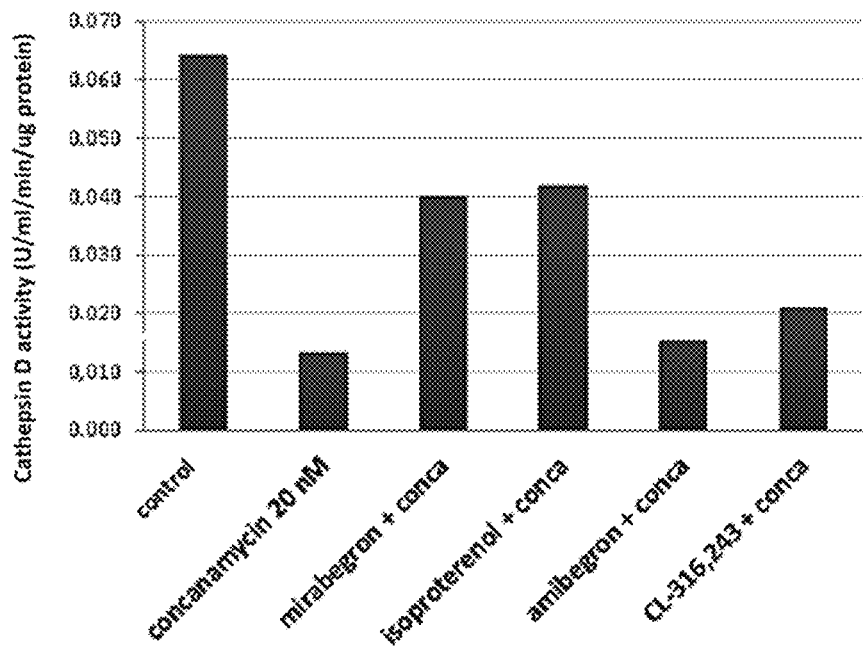
FIG. 2 is a histogram showing the effect of the adrenergic receptor agonists mirabegron, isoproterenol, amibegron and CL-316,243 on the cathepsin D activity of cells treated with concanamycin.

With the exception of amibegron, the treatment of RPE cells with all the molecules tested enables the partial restoration of cathepsin D activity (FIG. 2). In particular, the treatment with mirabegron multiplies 3-fold the activity of the enzyme (0.040 unit/ml of enzyme/min/µg of proteins) compared to the negative control represented by treatment with concanamycin (0.013 unit/ml of enzyme/min/µg of proteins).

Effect of Agonists on Lipofuscin Accumulation in RPE

In order to verify whether the different beta-adrenergic agonists are capable of also acting upon lipofuscin accumulation, we also tested them in a cell model wherein this accumulation is induced by treating RPE cells with oxidised OS by UV exposure every two days. The agonists were added at 10 µM to the culture medium at the time of the OS treatments. The lipofuscin accumulation was measured after two weeks of co-treatment by measuring the autofluorescence of the cells.

Figure 3:
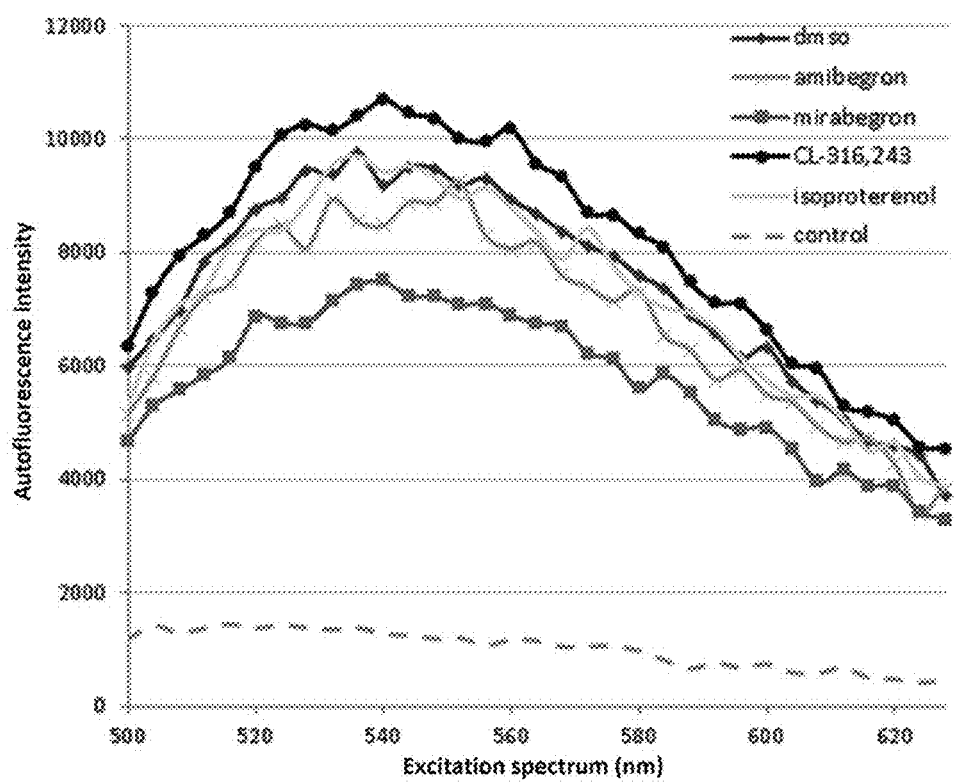
FIG. 3 is a graph showing the autofluorescence intensity of lipofuscin after two weeks of co-treatment of RPE cells with oxidised outer segments and with the adrenergic receptor agonists amibegron, mirabegron, CL-316,243 and isoproterenol. Cells co-treated with oxidised outer segments and with DMSO serve as controls.

The results demonstrate that, in two weeks, only mirabegron is capable of reducing the accumulation of lipofuscin by RPE cells by almost 20% (FIG. 3).

The invention claimed is:

1. A method for treating a retinal disease in a subject in need thereof, comprising administering to the subject mirabegron or a pharmaceutically acceptable salt or solvate thereof, wherein said retinal disease is age-related macular degeneration, Stargardt disease or pigmentary retinitis.

2. The method according to claim 1, wherein said retinal disease is age-related macular degeneration.

3. The method according to claim 1, wherein said retinal disease is atrophic age-related macular degeneration.

4. The method according to claim 1, wherein mirabegron or a pharmaceutically acceptable salt or solvate thereof is comprised in a pharmaceutical composition further comprising at least one pharmaceutically acceptable vehicle.

5. The method according to claim 1, wherein mirabegron or a pharmaceutically acceptable salt or solvate thereof is administered to the subject in need thereof orally or topically.

* * * * *